(12) United States Patent
Amouri

(10) Patent No.: US 8,367,723 B2
(45) Date of Patent: Feb. 5, 2013

(54) SELENOQUINONE-DERIVED ACTIVE ORGANOMETALLIC COMPLEXES, METHODS FOR SYNTHESIZING SAME, AND USES THEREOF

(75) Inventor: Haniel H. Amouri, Paris (FR)

(73) Assignee: Centre National de la Recherche Scientifique—CNRS, Paris Cedex (FR)

( * ) Notice: Subject to any disclaimer, the term of this patent is extended or adjusted under 35 U.S.C. 154(b) by 0 days.

(21) Appl. No.: 13/383,563

(22) PCT Filed: Jul. 22, 2010

(86) PCT No.: PCT/FR2010/051555
§ 371 (c)(1),
(2), (4) Date: Mar. 23, 2012

(87) PCT Pub. No.: WO2011/010072
PCT Pub. Date: Jan. 27, 2011

(65) Prior Publication Data
US 2012/0184611 A1    Jul. 19, 2012

(30) Foreign Application Priority Data
Jul. 23, 2009    (FR) .................................... 09 03641

(51) Int. Cl.
*A61K 31/28*    (2006.01)
*C07F 17/02*    (2006.01)

(52) U.S. Cl. ......................................... 514/492; 552/294
(58) Field of Classification Search .................. 552/294; 514/492
See application file for complete search history.

(56) References Cited

U.S. PATENT DOCUMENTS
5,760,266 A    6/1998    Eaton et al.

FOREIGN PATENT DOCUMENTS
ES    2 323 523 A1    7/2009
JP    7-089855 A    4/1995

OTHER PUBLICATIONS

J. Moussa et al., "Unprecedented pi-Bonded Rhodio- and Iridio-o-Benzoquinones as Organometallic Linkers for the Design of Chiral Octohedral Bimetallic Assemblies", Organometallics, Jan. 2, 2009, vol. 28, pp. 397-404.
E.J. Miller et al., "n5-C5(CH3)5 vs. n5-C5H5. A Comparison of Electronic Influences for Metallocenes with fac-a3b2c, fac-a3b3, and cis-a3b2 Ligand Geometry Based on 59C0 NQR Spectroscopy", Organometallics, 1985, vol. 4, pp. 533-538.
S. Nagao et al., "Synthesis of diiridium complexes with two bridging tetrachalcogenide ligands [{1r(nu5-C5Me5)}2(mu-E4)2] (E=Se or S) and their reactions with alkynes forming mono- or di-nuclear dichalcogenolene complexes", DALTON, 2000, pp. 3546-3553.

*Primary Examiner* — Porfirio Nazario Gonzalez
(74) *Attorney, Agent, or Firm* — Arent Fox LLP

(57) ABSTRACT

The present invention relates to the synthesis of novel biologically active selenoquinone-derived organometallic complexes, and to the uses thereof in the context of preventing or treating cancer.

16 Claims, 1 Drawing Sheet

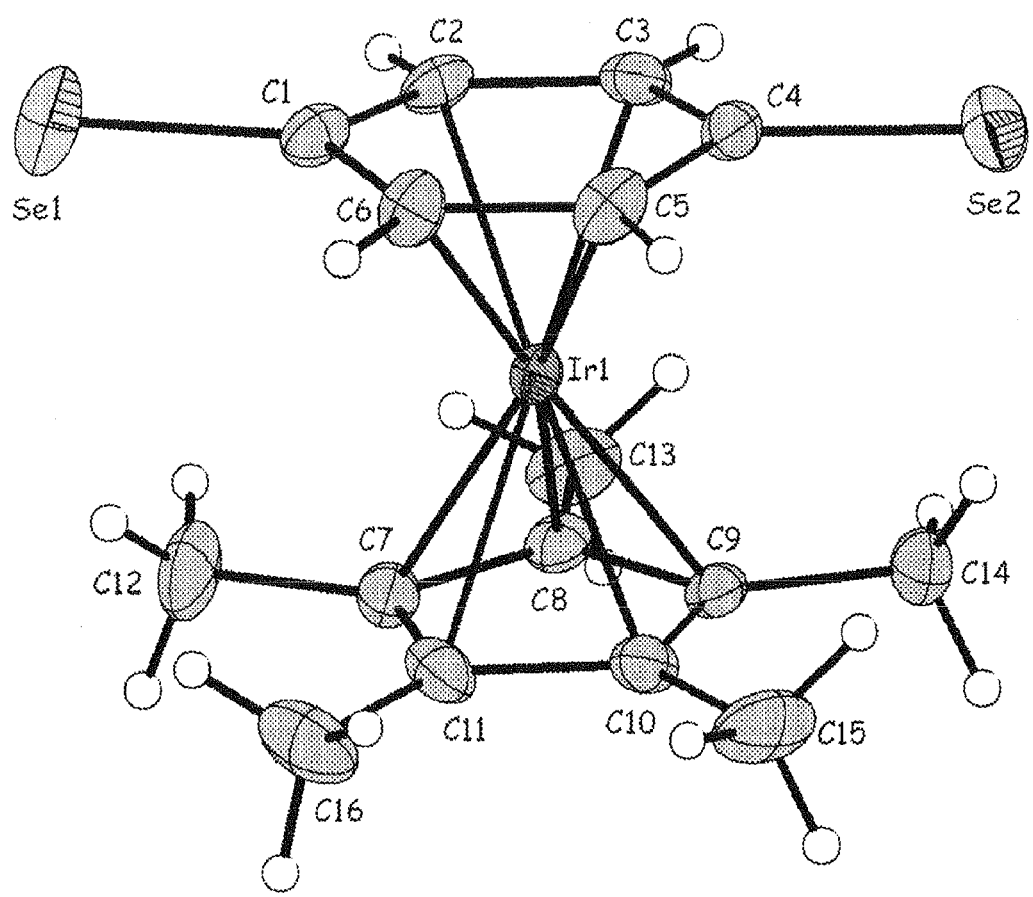

SELENOQUINONE-DERIVED ACTIVE ORGANOMETALLIC COMPLEXES, METHODS FOR SYNTHESIZING SAME, AND USES THEREOF

CROSS-REFERENCE TO RELATED APPLICATIONS

This application is a National Stage entry of International Application No. PCT/FR2010/051555, filed Jul. 22, 2010, which claims priority to French patent application Ser. No. 09/03641 filed Jul. 23, 2009, the disclosure of the prior application are incorporated in their entirety by reference.

TECHNICAL FIELD

The present invention relates to the synthesis of biologically active organometallic complexes from selenoquinone.

These complexes have applications in the field of the prevention or treatment of diseases involving abnormal cell proliferation, in particular cancer.

In the description below, the references between square brackets ([ ]) refer to the list of the references presented at the end of the text.

STATE OF THE ART

Quinones represent a class of compounds playing an important role in chemistry and biology [1]. For example, vitamin K has a quinone function group in its structure (naphthoquinone) [2] and has antihemorrhagic properties, lawsone is a naphthoquinone produced in the natural state by a plant originating in Arabia (*Lawsonia inermis*), better known under the name of henna and used in particular to dye wool and silk, or the hair, alizarin is a natural dye with a red color synthesized by W. H. Perkin in 1868.

The biological activity of quinones is often associated with their electron transfer levels and with their oxidation/reduction potential [3]. Quinone/hydroquinone redox pairs have been widely used in electrochemical studies due to their rapid availability and because they exhibit a good electrochemical behavior [4].

Hydroquinone in aqueous solution has many uses, mainly due to its action as reducing agent. It is one of the major components in the development of photographs where, in the presence of Metol (or 4-(methylamino)phenol), it reduces the exposed silver salts, which are invisible, to metallic silver. In human medicine, hydroquinone has been used in application on the skin in order to reduce the color thereof without the risk of dermatoses via the reduction in the synthesis of melanin by inhibition of the formation of the enzyme tyrosinase. However, this use has been banned in the European Union since February 2001 due to fears of carcinogenic effects and "serious complications".

There currently exist very few examples of organometallic complexes where the hydroquinone or the quinone act as π-bonded ligands [5,6]. Thus, the chromium analog $Cr(CO)_3(\eta^6\text{-hydroquinone})$ has been reported as thermally unstable and air-sensitive, and for this reason could not be isolated [7]. Consequently, the nature of the metal and the auxiliary ligands appears to play a major role in the stabilization of these quinone/hydroquinone complexes.

In 1998, the Inventors succeeded in synthesizing the first stable quinone/hydroquinone metal complexes: the stable iridium/hydroquinone complex $[(C_5Me_5)Ir(\eta^6\text{-hydroquinone})]^{2+}$ and the iridium/quinone complex $[(C_5Me_5)Ir(\eta^4\text{-quinone})]$ [8]. They then succeeded, in 2004, in synthesizing rhodium/hydroquinone and rhodium/quinone complexes $[(C_5Me_5)Rh(\eta^6\text{-hydroquinone})]^{2+}$ and $[(C_5Me_5)Rh(\eta^4\text{-quinone})]$ [9].

In contrast to benzoquinones (ortho- and para-), their sulfur analogs, dithiobenzoquinones (ortho- and para-), are highly unstable reactive intermediates and consequently remain very little studied, as is attested by the very small number of publications on this subject. The essential reason for the instability of dithiobenzoquinones is rooted in the high general lability of the C=S double bond in comparison with the C=O double bond [10]. However, in 2006 and 2007, the Inventors succeeded, by an innovatory synthetic process, in synthesizing stable dithioquinone organometallic complexes in the form of ortho- and para-isomers [12].

However, in contrast to the biological properties of free quinones, those of the organometallic complexes derived from quinone/hydroquinone and their sulfur derivatives have not been identified.

Mention may be made, among organometallic complexes whose biological properties have been demonstrated, of cisplatin or cis-diamminedichloroplatinum(II) (CDDP), which is a platinum-based complex used in the treatment of various cancers, such as sarcomas, carcinomas (small cell lung cancer, ovarian cancer, and the like) or lymphomas. It belongs, with carboplatin and oxaliplatin, to the category of the compounds which alkylate DNA. Cisplatin is an organometallic complex which selectively attaches to the purine bases of DNA (A or G) and brings about a variation in the local conformation of the DNA double strand. This deformation inhibits the replication and the transcription of the DNA to give RNA and in this way induces cell death. Different protein mechanisms for repairing with regard to the formation of cisplatin/DNA adducts exist and recognize some of the adducts formed. Research against cancer is based on the cytotoxicity of cisplatin, while looking for novel means of targeting the toxicity onto cancer cells (devoid of certain mechanisms for controlling DNA) [14].

Cancer is one of the greatest causes of mortality and consequently one of the most serious public health problems in the world today. Numerous medicaments have been and are being developed. However, these medicaments do not make it possible to treat all cases successfully. Moreover, the drugs used in the context of chemotherapies can exhibit undesirable side effects and an effectiveness and/or specificity of action with regard to cancer cells which is inadequate.

In particular, cisplatin exhibits significant toxic side effects and can result in allergies, gastrointestinal disorders (nausea, vomiting, ulceration of the digestive tract), hematological disorders (fall in the number of red blood cells, white blood cells and platelets), renal disorders, auditory disorders (buzzing in the ear, hypoacusis for high frequencies, major difficulty in telling where sound is coming from, a loss in selectivity of the ear) or neurological disorders (paresthesia of the extremities with more or less permanent pins and needles, and then an acute decrease in sensitivity resulting in more or less marked ataxia) [15]. Moreover, the salt, $K_2PtCl_4$, used in the preparation of cisplatin is twice as expensive as other corresponding metal salts, for example the iridium salt $IrCl_3 \cdot xH_2O$.

It is thus an aim of the present invention to provide novel organometallic complexes which are stable and inexpensive, which exhibit an anticancer activity and/or which exhibit reduced side effects. It is also an aim of the present invention to provide means for the production of such complexes.

DESCRIPTION OF THE INVENTION

The Inventors of the present invention have unexpectedly developed a novel synthetic process which is reliable, inexpensive, reproducible and easy to carry out, which makes it possible to obtain first stable organometallic complexes derived from selenoquinone. They also discovered, entirely unexpectedly, that these complexes, which until now had not been isolated or characterized, exhibit biological (cytotoxicity) properties at least equivalent to those of cisplatin, for this reason making it possible to use them in the context of the prevention or treatment of diseases involving abnormal cell proliferation, in particular cancer.

The term "stable" is preferably understood to mean complexes which are sufficiently stable to allow them to be prepared and which remain intact for a period of time sufficient to allow them to be detected and preferably for a period of time sufficient to be able to be used in the context of the prevention or treatment of diseases involving abnormal cell proliferation, in particular cancer.

The term "abnormal cell proliferation" is understood to mean a proliferation which is independent of the normal regulating mechanisms, for example the halting of cell proliferation due to the involvement of apoptosis (programmed cell death).

The present invention thus relates firstly to an isolated organometallic compound of general formula (I):

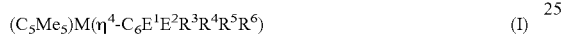

$(C_5Me_5)M(\eta^4-C_6E^1E^2R^3R^4R^5R^6)$     (I)

or a pharmaceutically acceptable salt of the latter;
in which:
M represents a metal Ru, Co, Rh or Ir;
$E^1$ represents an oxygen, sulfur or selenium atom;
$E^2$ represents a selenium atom;
$R^3$, $R^4$, $R^5$ and $R^6$ represent, independently of one another, a hydrogen atom, a hydroxyl group, a $C_{1-8}$ alkyl group, a $C_{2-8}$ alkenyl group, a $C_{2-8}$ alkynyl group, a $C_{1-6}$ alkoxyl group, a $C_{6-14}$ aryl group or an R'—NH amine group where R' represents a hydrogen atom, a $C_{1-8}$ alkyl group, a $C_{2-8}$ alkenyl group or a $C_{2-8}$ alkynyl group.

The term "isolated" is generally understood to mean a compound which is (i) separated from at least one compound with which it is associated naturally and/or (ii) produced, prepared or manufactured by the hand of man.

The term "$\eta^4$" is understood to mean the "hapticity of 4", that is to say that the arene is bonded to the metal via four bonds.

The alkyl groups can comprise from 1 to 8 carbon atoms, preferably from 1 to 6 carbon atoms and in particular from 1 to 2 carbon atoms.

The alkenyl groups can comprise from 2 to 8 carbon atoms, preferably from 2 to 6 carbon atoms and in particular from 2 to 4 carbon atoms. In addition, they can comprise one or more double bond(s).

The alkynyl groups can comprise from 2 to 8 carbon atoms, preferably from 2 to 6 carbon atoms and in particular from 2 to 4 carbon atoms. In addition, they can comprise one or more triple bond(s).

The alkoxyl groups can comprise from 1 to 6 carbon atoms, preferably from 1 to 4 carbon atoms and in particular from 1 to 2 carbon atoms.

The aryl groups denote a mono-, bi- or tricyclic hydrocarbon system comprising one, two or three rings satisfying the Huckel aromaticity rule. For example, an aryl radical can be a phenyl, naphthyl, tetrahydronaphthyl, indanyl or indenyl group and similar radicals. The aryl groups can comprise from 6 to 14 carbon atoms and in particular from 6 to 10 carbon atoms.

Unless otherwise mentioned, the alkyl, alkenyl, alkynyl or alkoxyl groups can be linear, branched or cyclic.

According to the present invention, $E^1$ and $E^2$ each represent a selenium atom and $R^3$, $R^4$, $R^5$ and $R^6$ are as defined above; preferably, at least one of them represents a $C_{1-8}$ alkyl group, very preferably a methyl group. For example, $E^1$ and $E^2$ each represent a selenium atom, $R^3$ and $R^5$ each represent a hydrogen atom and $R^4$ and $R^6$ each represent a methyl group.

According to the present invention, $E^1$ and $E^2$ each represent a selenium atom and $R^3$, $R^4$, $R^5$ and $R^6$ each represent a hydrogen atom.

According to the present invention, $E^1$ represents a sulfur or oxygen atom, preferably an oxygen atom, $E^2$ represents a selenium atom and $R^3$, $R^4$, $R^5$ and $R^6$ each represent a hydrogen atom.

According to the present invention, M represents Ir.

According to the present invention, in organometallic complexes of the present invention, $E^1$ and $E^2$ are in the ortho- or para-position.

According to the present invention, said complexes have one of the following structures:

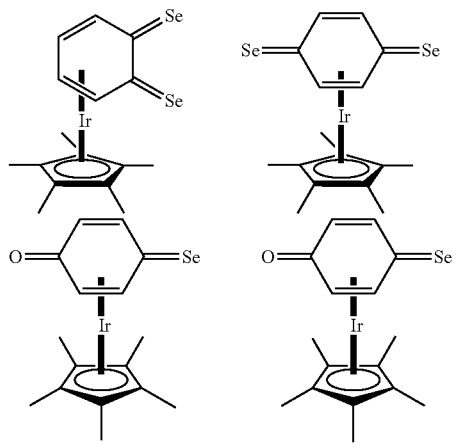

In addition, the Inventors have demonstrated that the organometallic complexes of the present invention have biological (cytotoxicity) properties at least equivalent to those of cisplatin.

Thus, according to a specific embodiment of the present invention, the organometallic complexes of the present invention can be used as medicament, in particular for the production of a medicament intended for the treatment of cancer.

The organometallic complexes of the present invention can, if appropriate, be in the salt solvated form or in the form of other physiologically acceptable derivatives. The salts and the solvents which are acceptable for pharmaceutical use are generally those in which the associated counterion or solvent is pharmaceutically acceptable.

The salts which can be used can be organic or inorganic acids or bases. Mention may be made, among acceptable acid addition salts, of those formed from hydrochloric, hydrobromic, sulfuric, citric, tartaric, phosphoric, lactic, pyruvic, acetic, trifluoroacetic, phenylacetic or triphenylacetic acid.

Mention may also be made, among acceptable basic salts, of salts of alkali metals, such as sodium or potassium, salts of alkaline earth metals, such as calcium and magnesium, and salts formed from organic bases, such as mono-, di- or trisubstituted amines.

The present invention also relates to a pharmaceutical composition comprising, as active principle, at least one compound according to the present invention in a pharmaceutically acceptable vehicle.

In particular, the pharmaceutical composition can be an anticancer composition.

In the pharmaceutical composition, the compounds are employed in an effective amount. This will be determined by a person skilled in the art according to various parameters, in particular with respect to the substance used, the age, weight and physical condition of the patient, the method of administration and the regime required. A person skilled in the art will be in a position to determine the method of administration and the dosage for each patient.

Very particularly, the compound according to the invention can be administered at a dose ranging from 0.1 to 5000 mg per day and per patient.

The pharmaceutical composition can comprise an amount of compound according to the invention ranging from 0.1 mg to 5 g.

The pharmaceutical composition can be administered in any topical or systemic form, in particular in the parenteral or enteral form.

When the composition or the medicament is administered by the enteral route, it can be provided in the form of tablets, including sugar-coated tablets, hard gelatin capsules, syrups, suspensions, solutions, powders, granules, emulsions or microspheres.

In the case of administration by the parenteral route, the composition can be provided in the form of solutions or suspensions for infusion or for injection.

In addition, the composition can comprise at least one additive chosen in particular from coloring agents, flavoring agents and preservatives. Of course, a person skilled in the art will take care to choose the additive or additives so that the advantageous properties intrinsically attached to the invention are not, or not substantially, detrimentally affected by the envisaged addition.

According to a specific embodiment, the composition according to the invention can additionally comprise another compound intended to treat cancer. Mention may be made, among the compounds which can be used according to the invention, of doxorubicin, the commercial name of which is Adriamycin®, epothilone, paclitaxel, the commercial name of which is Taxol®, and cisplatin.

According to yet another of its aspects, the subject matter of the invention is the use of at least one organometallic complex of the present invention in the preparation of a pharmaceutical composition intended to treat and/or prevent a disease involving abnormal cell proliferation, in particular a cancer.

Said composition can be intended for human and/or veterinary medicine and it can in particular be intended to treat or prevent at least one cancer chosen, for example, from pancreatic cancer, oropharyngeal cancer, stomach cancer, esophageal cancer, colorectal cancer, brain cancer, in particular gliomas, ovarian cancer, liver cancer, kidney cancer, laryngeal cancer, thyroid cancer, lung cancer, bone cancer, multiple myelomas, mesotheliomas and melanomas, skin cancer, breast cancer, prostate cancer, bladder cancer, uterine cancer, testicular cancer, non-Hodgkin's lymphoma, leukemia, Hodgkin's disease and soft tissue cancers, as well as secondary metastatic occurrences of the abovementioned cancers.

The present invention also relates to a process for the synthesis of the organometallic complexes of the present invention which comprises a nucleophilic attack on the compound of following formula (II):

$$[(C_5Me_5)M(\eta^6-C_6X^1X^2R^3R^4R^5R^6)][Z]_2 \quad (II)$$

in which:
M, $R^3$, $R^4$, $R^5$ and $R^6$ are as defined above;
$X^1$ and $X^2$ are identical or different and each represent a halogen atom Cl, Br or I;

Z represents a counteranion $BF_4^-$, $PF_6^-$ or $CF_3SO_3^-$ (or OTf−), by at least one nucleophile $Y_2Se$, where Y is an alkali metal cation.

According to a specific embodiment of the synthetic process of the present invention, the nucleophilic attack is carried out with sodium selenide ($Na_2Se$).

Other advantages may further appear to a person skilled in the art on reading the following examples, illustrated by the appended figures, given by way of illustration.

BRIEF DESCRIPTION OF THE FIGURES

FIG. 1 represents the crystallographic structure of the organometallic complex [(C_5Me_5)Ir($\eta^4$-p-diselenobenzoquinone)] (8).

EXAMPLES

Example 1

Synthesis of Iridium/Selenoquinone Complexes 7-8

Three different synthetic processes exist for preparing quinone complexes (1-4), dithioquinone complexes (5,6) and mono- and diselenoquinone complexes (7, 8, 9, 10). The synthesis of the families 1-6 is well known in the art [13], in contrast to that of the mono- and diselenoquinone complexes, which constitutes a subject matter of the present invention.

1—Synthesis of the Iridium/Quinone Complexes (1-4)

para-Quinone organometallic complexes were prepared by direct treatment of hydroquinone and the solvated compound $[(C_5Me_5)M(solvent)_3]^{2+}$, where M=Rh or Ir, prepared in situ, followed by a subsequent deprotonation by a base, in order to obtain the para-quinone organometallic complexes p-[(C_5Me_5)M($\eta^4$-quinone)], where M=Rh (2) or Ir (4) [8-9].

Similarly, ortho-quinone organometallic complexes were obtained by treatment of catechol with the solvated compound $[(C_5Me_5)M(solvent)_3]^{2+}$, where M=Rh or Ir, in the presence of $BF_3 \cdot 2H_2O$ as activator of the arene, in order to provide for the bonding of the metal fragment to the arene ring, followed by a deprotonation, in order to obtain the ortho-quinone organometallic complexes o-[(C_5Me_5)M($\eta^4$-quinone)], where M=Rh (1) or Ir (3) [11].

2—Synthesis of the Iridium/Dithioquinone Complexes (5,6)

The sulfur homologs of hydroquinone and catechol were obtained by a different synthetic process from above. Thus, the air-sensitive ortho- and para-dichlorobenzene organometallic complexes were prepared and isolated in the form of white microcrystalline compounds. A treatment of said compounds with sodium hydrosulfide produced the thioquinone organometallic complexes in the form of ortho-(5) and para-(6) isomers [12].

3—Synthesis of the Iridium/Mono- and Diselenoquinone Complexes (7, 8, 9, 10)

The ortho- and para-selenoquinone organometallic complexes were synthesized according to the following reaction scheme:

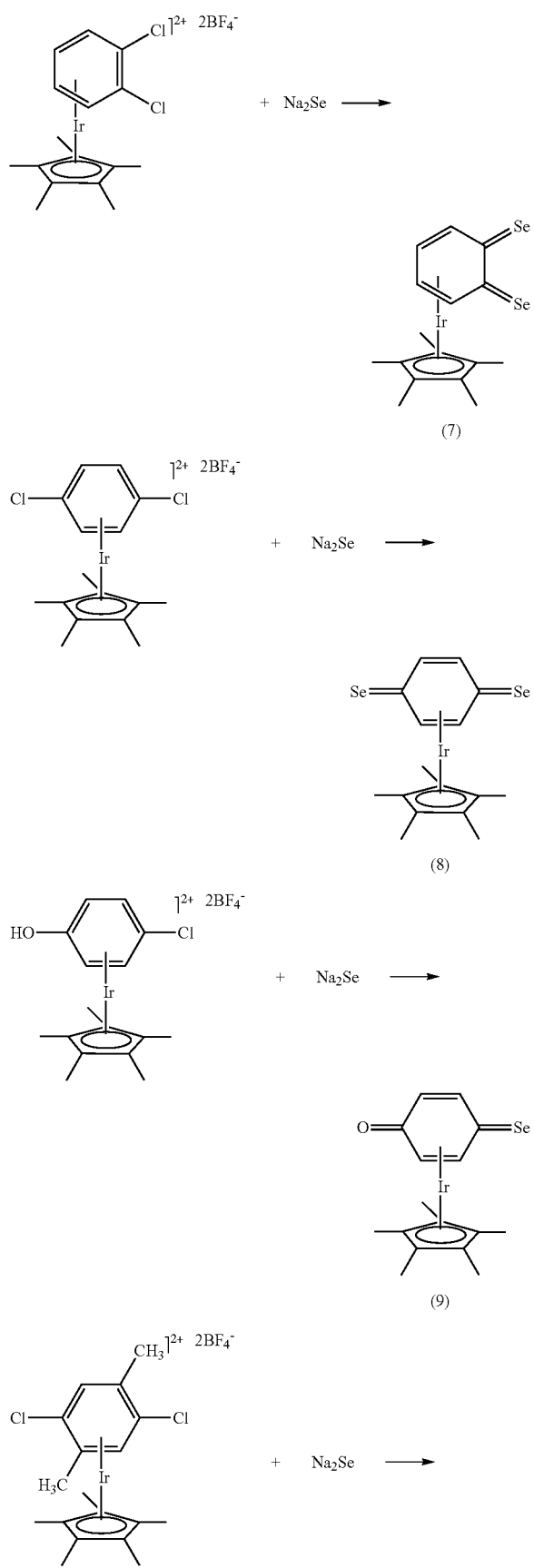
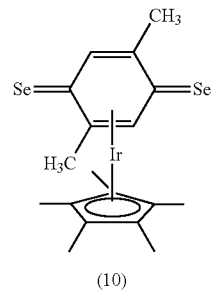

The first stage of this synthetic scheme involves the preparation of air-sensitive halogenated organometallic complexes of ortho- and para-dichlorobenzene [(C$_5$Me$_5$)Ir(η$^6$-C$_6$H$_4$Cl$_2$)][BF$_4$]$_2$, air-sensitive halogenated organometallic complex of para-monochlorohydroxybenzene p-[(C$_5$Me$_5$)Ir(η$^6$-C$_6$H$_4$ClOH)][BF$_4$]$_2$ and air-sensitive halogenated organometallic complex of para-dichlorodimethylbenzene p-[(C$_5$Me$_5$)Ir(η$^6$-C$_6$H$_2$Cl$_2$(CH$_3$)$_2$)][BF$_4$]$_2$.

3-1—Synthesis of the Complex p-[(C$_5$Me$_5$)Ir(η$^4$-diselenobenzoquinone)] (8)

A colored solution of p-[(C$_5$Me$_5$)Ir(η$^6$-C$_6$H$_4$Cl$_2$)][BF$_4$]$_2$ (340 mg, 0.52 mmol) in CH$_3$CN distilled at the time of use (10 ml) was added to a Schlenk tube containing anhydrous Na$_2$Se (650 mg, 5.2 mmol) stored under an argon atmosphere. The reaction mixture rapidly changed to orange in color with the formation of a precipitate (NaCl and NaBF$_4$). The reaction was maintained for 20 minutes and then the solvent was removed under vacuum in order to provide an orangey black residue. Subsequently, the compound was extracted using 50 ml of distilled CH$_2$Cl$_2$ and filtered under an argon atmosphere through a sintered glass filter equipped with cotton wool/celite/cotton wool to give a bright orange color. The solvent was removed under vacuum to give an orange microcrystalline powder identified as p-[(C$_5$Me$_5$)Ir(η$^4$-C$_6$H$_4$Se$_2$)][BF$_4$]$_2$ (241 mg, 0.49 mmol). Yield 95%.

The compound (8) is stable and can be stored for a long period under an argon atmosphere. The compound (8) is soluble in CH$_2$Cl$_2$, MeOH and acetone and in the majority of polar organic solvents.

IR (ATR), ν cm$^{-1}$: 2990, 1467, 1421, 1380, 1272, 1053, 1024, 731, 704, 633, 431, 353.

$^1$H NMR (400 MHz, CD$_2$Cl$_2$), δ (ppm): 1.89 (15H, s, η-C$_5$Me$_5$); 6.26 (4H, s, CH p-diselenobenzoquinone).

$^{13}$C{$^1$H} NMR (100 MHz, CD$_2$Cl$_2$), δ (ppm): 6.86 (CH$_3$, s, η-C$_5$Me$_5$); 96.83 (CH, s, p-diselenoquinone); 96.97 (C=C, s, η-C$_5$Me$_5$); 132.96 (C—Se, s, diselenoquinone). $^{77}$Se{$^1$H} NMR (400 MHz, CD$_2$Cl$_2$), δ (ppm): 296 (2Se, s, C—Se).

3-2—Synthesis of the Complex o-[(C$_5$Me$_5$)Ir(η$^4$-diselenobenzoquinone)] (7)

The compound (7) was prepared in a similar way to that of the compound (8). The molecule is somewhat less stable than the para-isomer. Studies are currently underway to optimize the method of synthesis.

IR (ATR), ν cm$^{-1}$: 3373, 2912, 1585, 1467, 1378, 1258, 1019, 885, 800, 728, 696, 636, 608, 550, 518, 464, 386, 308.

3-3—Synthesis of the Complex p-[(C$_5$Me$_5$)Ir(η$^4$-monoselenobenzoquinone)] (9)

The compound (9) was prepared in a similar way to that of the compound (8) but starting from the monochlorinated organometallic complex p-[$(C_5Me_5)Ir(\eta^6-C_6H_4ClOH)$][$BF_4$]$_2$ and was obtained with a yield of 90%. $^1$H NMR (400 MHz, $CD_2Cl_2$) δ (ppm): 1.92 (15H, s, η-$C_5Me_5$); 5.32 (2H, d, 6 Hz, CH p-diselenobenzoquinone); 6.29 (2H, d, 6 Hz, CH p-diselenobenzoquinone). IR (ATR), ν cm$^{-1}$: 2964, 2917, 1630, 1605, 1468, 1385, 1259, 1024, 802, 691, 636, 606, 557, 518, 452, 429.

3-4—Synthesis of the Complex p-[$(C_5Me_5)Ir(\eta^4$-2, 5-dimethyldiselenobenzoquinone)] (10)

The compound (10) was prepared in a similar way to that of the complex (8) but starting from p-[$(C_5Me_5)Ir(\eta^6-C_6H_2Cl_2(CH_3)_2)$][$BF_4$]$_2$ and was obtained with a yield of 90%.
$^1$H NMR (400 MHz, $d_4$-MeOH), δ (ppm): 1.79 (15H, s, η-$C_5Me_5$); 2.51 (6H, s, $CH_3$—); 6.78 (2H, s, CH p-diselenobenzoquinone). IR (ATR), ν cm$^{-1}$: 3616, 3568, 1637, 1467, 1406, 1381, 1259, 1043, 893, 742, 634, 606, 522, 461.

Example 2

Biological Properties of the Quinone, Thioquinone and Selenoquinone Organometallic Complexes (1-10)

The biological (cytotoxicity) properties of the complexes synthesized above were tested on A2780 and A2780cisR (cisplatin-resistant) ovarian cancer cells according to a conventional procedure described below, and the IC$_{50}$ values obtained were compared with those obtained under the same conditions with the cisplatin complex Pt ($NH_3$)$_2$Cl$_2$.

The A2780 and A2780cisR ovarian cancer cell lines were obtained from The European Collection of Cell Cultures (ECACC) (Salisbury, UK). The cells were cultured in RPMI medium comprising glucose, 5% of fetal calf serum (FCS) and antibiotics, at 37° C. and 5% $CO_2$.

The cytotoxicity was determined using the MTT (3-(4,5-dimethyl-2-thiazolyl)-2,5-diphenyl-2H-tetrazolium bromide) test (MOSMANN, 1983).

The cells were distributed in 96-well plates, as monolayers, with 100 µl of solution (approximately 20 000 cells) per well, and were preincubated for 24 hours in a medium supplemented with 10% of FCS.

The compounds were prepared in DMSO solution, were then dissolved in the culture medium and were successively diluted to the appropriate concentration, in order to obtain a final DMSO concentration of 0.5%. 100 µl of solution of these compounds were added to each well and the plates were incubated for 72 hours. Subsequently, MTT (5 mg/ml) was added to the cells and the plates were incubated for 2 hours. The culture medium was removed by suction and the purple formazan crystals formed by the mitochondrial dehydrogenase activity of the living cells were dissolved in DMSO.

The optical density, which is directly proportional to the number of living cells, was quantified at 540 nm using a multiwell plate reader and the fraction of living cells was quantified from the absorbance of untreated control cells. Evaluation was carried out from two independent experiments, each comprising 3 microcultures per concentration level.

The IC$_{50}$ values obtained are presented in table 1 below.

TABLE 1

| Name of the complex | IC$_{50}$ (µmol) |
|---|---|
| o-[$(C_5Me_5)Rh(\eta^4$-benzoquinone)] (1) | >400 |
| p-[$(C_5Me_5)Rh(\eta^4$-benzoquinone)] (2) | >400 |
| o-[$(C_5Me_5)Ir(\eta^4$-benzoquinone)] (3) | >400 |

TABLE 1-continued

| Name of the complex | IC$_{50}$ (µmol) |
|---|---|
| p-[$(C_5Me_5)Ir(\eta^4$-benzoquinone)] (4) | 93 |
| o-[$(C_5Me_5)Ir(\eta^4$-dithiobenzoquinone)] (5) | 49 |
| p-[$(C_5Me_5)Ir(\eta^4$-dithiobenzoquinone)] (6) | 154 |
| o-[$(C_5Me_5)Ir(\eta^4$-diselenobenzoquinone)] (7) | / |
| p-[$(C_5Me_5)Ir(\eta^4$-diselenobenzoquinone)] (8) | 5 |
| p-[$(C_5Me_5)Ir(\eta^4$-monoselenobenzoquinone)] (9) | 12.3 |
| p-[$(C_5Me_5)Ir(\eta^4$-2,5-dimethyldiselenobenzoquinone)] (10) | 6.2 |
| cis-[Pt($NH_3$)$_2$Cl$_2$] | 3 |

The results show that the dithiobenzoquinone complexes and in particular the monoselenoquinone and diselenoquinone organometallic complexes (8-10) have significant biological (cytotoxicity) properties equivalent to those of the cisplatin compound with regard to the A2780 ovarian cancer cell line.

In addition, in an entirely noteworthy way, the two complexes 9 and 10 have superior cytotoxic properties to cisplatin with regard to the A2780cisR (cisplatin-resistant) ovarian cancer cell line, with an IC$_{50}$ value of 8.4 µmol for compound 9 and an IC$_{50}$ value of 7.3 µmol for compound 10, whereas the IC$_{50}$ value of the cis-[Pt($NH_3$)$_2$Cl$_2$] complex for the A2780cisR cell line is 25 µmol.

The organometallic complexes of the invention can thus be used in the context of the prevention and/or treatment of diseases involving abnormal cell proliferation, in particular cancer.

Their use will be very particularly beneficial in the context of diseases for which a treatment based on cisplatin has proved to be not very effective or indeed even ineffective.

Example 3

Crystallography of the Diselenobenzoquinone Complex p-[$(C_5Me_5)Ir(\eta^4$-diselenobenzoquinone)] (8)

Crystals of the biologically active molecule [($C_5Me_5$)Ir ($\eta^4$-p-diselenobenzoquinone)] (8) were obtained by slow diffusion of ethyl ether into a methanol solution of this complex. X-ray diffraction made it possible to resolve the structure.

To do this, the structure was resolved by direct methods using the SIR92 program [18] and refined anisotropically by the full matrix least squares method using the SHELXL-97 software package [19].

The structure resolved by X-ray diffraction (FIG. 1) shows that this complex crystallizes in a monoclinic mesh with the P2$_1$/c space group and Z=4.

The analysis of the distances and angles [table 2: selection of distances (Å) and angles) (°)] made it possible to confirm the formation of the p-diselenobenzoquinone. This data indicated that the p-diselenobenzoquinone is coordinated to the iridium via the 4 diene carbon atoms C(2), C(3), C(5) and C(6). This is because the Ir(1)-C(1) and Ir(1)-C(4) distances are longer than the Ir(1)-C(2), Ir(1)-C(3), Ir(1)-C(5) and Ir(1)-C(6) distances. Consequently, the p-diselenobenzoquinone has adopted a conformation slightly angled in the boat form. The dihedral angle between the [C(2)C(3)C(5)C(6)] and [C(2)C(1)C(6)] planes is equal to 7.04°. That between the [C(2)C(3)C(5)C(6)] and [C(3)C(4)C(5)] planes is equal to 5.94°. In addition, the C(1)-Se(1) and C(4)-Se(2) distances are equal to 1.876 Å and 1.865 Å respectively. These distances are in agreement with a double rather than single nature for the bond between C and Se in comparison with the C—Se distance found for Se—Ar (1.925 Å) [16] and the C=Se distance (1.88 Å) [17] encountered in the cobalt complex [CoCl$_2$ (C$_5$H$_8$N$_2$Se)$_2$].

TABLE 2

| Å (°) | | Å (°) | |
|---|---|---|---|
| Ir(1)—C(1) | 2.370 (8) | C(1)—Se(1) | 1.876 (10) |
| Ir(1)—C(2) | 2.229 (8) | C(4)—Se(2) | 1.865 (9) |
| Ir(1)—C(3) | 2.236 (6) | C(2)—C(1)—C(6) | 113.79 (7) |
| Ir(1)—C(4) | 2.349 (5) | C(3)—C(4)—C(5) | 113.74 (7) |
| Ir(1)—C(5) | 2.226 (7) | | |
| Ir(1)—C(6) | 2.239 (7) | | |

Furthermore, the examination of the structure at the level of the crystal showed that this complex forms stacks by π-π interactions between the molecules of the [(C$_5$Me$_5$)Ir((η$^4$-C$_6$H$_4$Se$_2$)]. Furthermore, the aromatic ring of the Cp* ligand interacts with the diene system of the p-diselenobenzoquinone of a neighboring molecule (d=3.563 Å). These interactions make possible the formation of a supramolecular chain, the cohesion of which is provided by the π-π stackings.

LIST OF THE REFERENCES

[1] (a) Larsen, P. L.: Clarke, C. F., Science, 2002, 295, 120. (b) Do, T. Q.; Hsu, A. Y.; Jonassen, T.; Lee, P. T.; Clarke, C. F., J. Biol. Chem., 2001, 276, 18161. (c) Steinberg-Yfrach, G.; Liddell, P. A.; Moore, A. L.; Gust, D.; Moore, T. A., Nature, 1997, 385, 239. (d) Cross, J. V.; Deak, J. C.; Rich, E. A.; Qian, Y.; Lewis, M.; Parrott, L. A.; Mochida, K.; Gustfason, D.; Vande Pol, S.; Templeton, D. J., J. Biol. Chem., 1999, 274, 31150.

[2] Lamson, D. W.; Plaza, S. M., Altern. Med. Rev., 2003, 8, 303.

[3] Voet, D.; Voet, J. B.; Pratt, C. W., Fundamentals of Biochemistry, Wiley: New York, 1999.

[4] (a) Parker, V., Chem. Commun., 1969, 716. (b) Eggins, B.; Chambers, J. Q., Chem. Commun., 1969, 232.

[5] (a) Liebeskind, L. S.; Jewell, C. F. Jr., J. Organomet. Chem., 1985, 285, 305. (b) Jewell, C. F. Jr.; Liebeskind, L. S.; Williamson, M., J. Am. Chem. Soc., 1985, 107, 6715. (c) Cho, S. H.; Wirtz, K. R.; Liebeskind, L. S., Organometallics, 1990, 9, 3067.

[6] (a) Oh, M.; Carpenter, G. B.; Sweigart, D. A., Organometallics, 2002, 21, 1290. (b) Ura, Y.; Sato, Y.; Shiotsuki, M.; Suzuki, T.; Wada, K.; Kondo, T.; Mitsudo, T., Organometallics, 2003, 22, 77.

[7] (a) Wright, M. E.: J. Organomet, Chem., 1989, 376, 353. (b) Schumann, H.; Arif, A. M.; Richmond, T. G., Polyhedron, 1990, 9, 1677.

[8] (a) Le Bras, J.; Amouri, H.; Vaissermann, J., Organometallics, 1998, 17, 1116. (b) Le Bras, J.; Amouri, H.; Vaissermann, J., J. Organomet. Chem., 1998, 553, 483.

[9] Moussa, J.; Guyard-Duhayon, C.; Herson, P.; Amouri, H.; Rager, M. N.; Jutand, A., Organometallics, 2004, 23, 6231.

[10] (a) Bock, H., Mohmand, S.; Hirabayashi, T.; Maier, G.; Reisenauer, H. P., Chem. Ber., 1983, 116, 273. (b) Breitenstein, M.; Schulz, R.; Schweig, A., J. Org. Chem., 1982, 47, 1979.

[11] Moussa, J.; Rager, M. N.; Chamoreau, L.-M.: Ricard, L.; Amouri, H., Organometallics, 2009, 28, 397.

[12] (a) Moussa, J.; Lev, D. A.; Boubekeur, K.; Rager, M. N.; Amouri, H., Angew. Chem. Int. Ed., 2006, 45, 3854. (b) Moussa, J.; Rager, M. N.; Boubekeur, K.; Amouri H., Eur. J. Inorg. Chem., 2007, 2648.

[13] Moussa, J.; Amouri, H., Angew. Chem. Int. Ed., 2008, 47, 1372.

[14] Bellon S F.; Coleman J H.; Lippard S J., Biochem., 1991, 30, 8026.

[15] Reedijk J.; Eur. J. Inorg. Chem., 2009, 2009, 1283.

[16] J. M. White, J. B. Lambert, M. Spiniello, S. A. Jones, R. W. Gable, Chem. Eur. J., 2002, 8, 2799.

[17] D. J. Williams, T. A. Jones, E. D. Rice, K. J. Davis, J. A. Ritchie, W. T. Pennington, G. L. Schimek, Acta Cryst., 1997, C53, 837.

[18] A. Altomare, G. Cascarano, C. Giacovazzo and A. Guagliardi, J. Appl. Crystallogr., 1993, 26, 343.

[19] G. M. Sheldrick, Acta Cryst. A, 2008, 64, 112.

The invention claimed is:

1. An isolated organometallic complex of general formula (I):

$$(C_5Me_5)M(\eta^4\text{-}C_6E^1E^2R^3R^4R^5R^6) \qquad (I)$$

or a pharmaceutically acceptable salt of the latter;

in which:

M represents a metal Ru, Co, Rh or Ir;

$E^1$ represents an oxygen, sulfur or selenium atom;

$E^2$ represents a selenium atom;

$R^3$, $R^4$, $R^5$ and $R^6$ represent, independently of one another, a hydrogen atom, a hydroxyl group, a $C_{1-8}$ alkyl group, a $C_{2-8}$ alkenyl group, a $C_{2-8}$ alkynyl group, a $C_{1-6}$ alkoxyl group, a $C_{6-14}$ aryl group or an R'—NH amine group where R' represents a hydrogen atom, a $C_{1-8}$ alkyl group, a $C_{2-8}$ alkenyl group or a $C_{2-8}$ alkynyl group.

2. The complex as claimed in claim 1, where $E^1$ and $E^2$ each represent a selenium atom and $R^3$, $R^4$, $R^5$ and $R^6$ are as defined in claim 1.

3. The complex as claimed in claim 2, where at least one from $R^3$, $R^4$, $R^5$ and $R^6$ represents a $C_{1-8}$ alkyl group.

4. The complex as claimed in claim 3, where $R^3$ and $R^5$ each represent a hydrogen atom and $R^4$ and $R^6$ each represent a $C_{1-8}$ alkyl group.

5. The complex as claimed in claim 2, where $R^3$, $R^4$, $R^5$ and $R^6$ each represent a hydrogen atom.

6. The complex as claimed in claim 1, where $E^1$ represents a sulfur or oxygen atom, $E^2$ represents a selenium atom and $R^3$, $R^4$, $R^5$ and $R^6$ each represent a hydrogen atom.

7. The complex as claimed in claim 1, where M represents Ir.

8. The complex as claimed in claim 1, where $E^1$ and $E^2$ are in the ortho- or para-position.

9. The complex as claimed in claim 1, having one of the following structures:

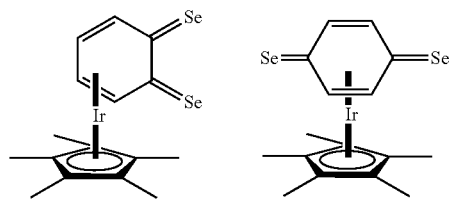

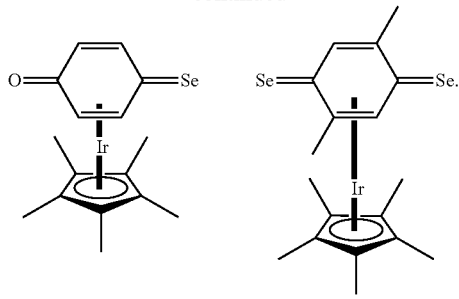

10. A pharmaceutical composition comprising, as active principle, at least one complex as claimed in claim 1 in a pharmaceutically acceptable vehicle.

11. A process for the synthesis of an isolated organometallic complex of general formula (I):

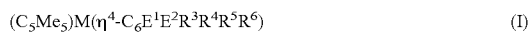

or a pharmaceutically acceptable salt of the latter;
in which;
M represents a metal Ru, Co, Rh or Ir;
$E^1$ represents an oxygen, sulfur or selenium atom;
$E^2$ represents a selenium atom;
$R^3$, $R^4$, $R^5$ and $R^6$ represent, independently of one another, a hydrogen atom, a hydroxyl group, a $C_{1-8}$ alkyl group, a $C_{2-8}$ alkenyl group, a $C_{2-8}$ alkynyl group, a $C_{1-6}$ alkoxyl group, a $C_{6-14}$ aryl group or an R'—NH amine group where R' represents a hydrogen atom, a $C_{1-8}$ alkyl group, a $C_{2-8}$ alkenyl group or a $C_{2-8}$ alkynyl group,
characterized in that it comprises a nucleophilic attack on the complex of following formula (II):

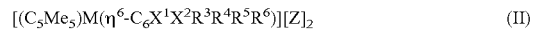

in which:
M, $R^3$, $R^4$, $R^5$ and $R^6$ are as defined above;
$X^1$ and $X^2$ are identical or different and each represent a halogen atom Cl, Br or I;
Z represents a counteranion $BF_4^-$, $PF_6^-$ or $CF_3SO_3^-$,
by at least one nucleophile $Y_2Se$, where Y is an alkali metal cation.

12. The synthetic process as claimed in claim 11, where the nucleophilic attack is carried out with sodium selenide ($Na_2Se$).

13. A method of treating cancer comprising administering to a patient in need thereof, a medicinally effective amount of the pharmaceutical composition as claimed in claim 10.

14. The complex as claimed in claim 2, where at least one from $R^3$, $R^4$, $R^5$ and $R^6$ represents a methyl group.

15. The complex as claimed in claim 3, where $R^3$ and $R^5$ each represents a hydrogen atom and $R^4$ and $R^6$ each represents a methyl group.

16. The complex as claimed in claim 1, where $E^1$ represents an oxygen atom, $E^2$ represents a selenium atom and $R^3$, $R^4$, $R^5$ and $R^6$ each represents a hydrogen atom.

* * * * *